(12) United States Patent
Rozema et al.

(10) Patent No.: US 7,816,337 B2
(45) Date of Patent: *Oct. 19, 2010

(54) REVERSIBLE ATTACHMENT OF A MEMBRANE ACTIVE POLYMER TO A POLYNUCLEOTIDE

(75) Inventors: David B. Rozema, Madison, WI (US); Darren Wakefield, Fitchburg, WI (US); Jon A Wolff, Fitchburg, WI (US); Kirk Ekena, Fitchburg, WI (US); James E. Hagstrom, Fitchburg, WI (US)

(73) Assignee: Roche Madison Inc., Madison, WI (US)

( * ) Notice: Subject to any disclaimer, the term of this patent is extended or adjusted under 35 U.S.C. 154(b) by 90 days.

This patent is subject to a terminal disclaimer.

(21) Appl. No.: 10/780,484

(22) Filed: Feb. 17, 2004

(65) Prior Publication Data

US 2004/0162260 A1    Aug. 19, 2004

Related U.S. Application Data

(60) Provisional application No. 60/448,209, filed on Feb. 18, 2003.

(51) Int. Cl.
 *A61K 31/70* (2006.01)
 *C12N 5/00* (2006.01)
 *C12N 15/00* (2006.01)
(52) U.S. Cl. .................. 514/44 R; 424/450; 435/325; 435/375; 435/455
(58) Field of Classification Search .............. None
See application file for complete search history.

(56) References Cited

U.S. PATENT DOCUMENTS

| 5,169,933 | A  | * | 12/1992 | Anderson et al. ........ 530/391.3 |
| 5,218,105 | A  | * | 6/1993  | Cook et al. .............. 536/25.31 |
| 5,453,461 | A  | * | 9/1995  | Heiliger et al. ............ 525/54.1 |
| 6,248,720 | B1 | * | 6/2001  | Mathiowitz et al. .......... 514/44 |
| 6,479,464 | B1 | * | 11/2002 | Haines et al. ................. 514/44 |
| 7,019,113 | B2 | * | 3/2006  | Rozema et al. ............. 530/333 |
| 7,087,770 | B2 | * | 8/2006  | Wolff et al. ................... 554/85 |
| 2001/0036926 | A1 | * | 11/2001 | Wolff et al. .................. 514/44 |
| 2002/0107330 | A1 | * | 8/2002  | Pinchuk et al. ............. 525/242 |
| 2004/0249122 | A1 | * | 12/2004 | Blazyk ...................... 530/324 |

FOREIGN PATENT DOCUMENTS

| WO | WO9114696 |    | 10/1991 |
| WO | WO9947173 |    | 9/1999 |
| WO | WO0075164 | A1 * | 12/2000 |
| WO | WO 0160162 | A2 * | 8/2001 |
| WO | WO03008628 |    | 1/2003 |
| WO | WO2004072249 |  | 8/2004 |

OTHER PUBLICATIONS

WO document is too voluminous, see US Patent Application US20040249122.*

* cited by examiner

*Primary Examiner*—Janet L Epps-Smith
(74) *Attorney, Agent, or Firm*—Kirk Ekens (57) ABSTRACT

Described is a process for delivering a biologically active compound to a cell by reversibly linking the compound to a membrane active polymer. In particular, polymer-polynucleotide conjugates are described. Methods for reversibly modifying the polymers to decrease cellular toxicity and improve efficacy are provided.

13 Claims, 3 Drawing Sheets

REVERSIBLE ATTACHMENT OF A MEMBRANE ACTIVE POLYMER TO A POLYNUCLEOTIDE

CROSS-REFERENCE TO RELATED APPLICATIONS

This application claims the benefit of prior U.S. Provisional Application Ser. No. 60/448,209 filed on Feb. 18, 2003.

FIELD OF INVENTION

This patent application concerns the delivery of polynucleotide to cells in vitro or cells in post-natal mammals using reversible molecular conjugates.

BACKGROUND OF THE INVENTION

The route of cellular entry for most conventional drugs is diffusion across the biological membrane. For this reason, drugs tend to be small (MW<500) and amphipathic, containing both hydrophobic and hydrophilic functionalities. These characteristics engender molecules with water solubility, while allowing them to cross the nonpolar lipid bilayer of the cell membrane. In contrast, the drugs used in antisense and gene therapies are relatively large hydrophilic polymers and are frequently highly negatively charged as well. Both of these physical characteristics preclude their direct diffusion across the cell membrane. For this reason, the major barrier to gene therapy and antisense therapy is the delivery of the drug to the cellular interior. This situation is in contrast to standard drug development in which the identification of the drug is the major barrier in development.

Gene or polynucleotide transfer to cells is an important technique for biological and medical research as well as potentially therapeutic applications. The polynucleotide needs to be transferred across the cell membrane and into the cell. Gene transfer methods currently being explored include viral vectors and non-viral methods.

Polymers can facilitate cellular entry of oligonucleotides. For instance, some polymers, such as polyethylenimine, are postulated to disrupt endosomal/lysosomal function through a proton sponge effect. Disruption of endosomal/lysosomal function has also been accomplished by linking endosomal or membrane disruptive agents such as fusion peptides or adenoviruses to the polycation or complex.

Polymers that are pH-sensitive have found broad application in the area of drug delivery because of their ability to exploit various physiological and intracellular pH gradients for the purpose of controlled release of drugs. pH sensitivity can be broadly defined as any change in polymer's physicochemical properties over a range of pH. Narrower definitions demand significant changes in the polymer's ability to retain or release a bioactive substance in a physiologically tolerated pH range (typically pH 5.5-8).

SUMMARY OF THE INVENTION

In a preferred embodiment, we describe cleavable covalent membrane active polymer-polynucleotide conjugates for delivery of polynucleotides to cells. The polynucleotide may be DNA, RNA, or synthetic polynucleotides or oligonucleotides. The cell may be in vitro or in vivo. A preferred polymer is an amphiphilic polyvinylether. A polyvinylether polymer may contain monomer subunits selected from the list comprising: alkyl vinylethers, positively charged vinylethers, negatively charged vinylethers, aryl vinylethers, and polyethyleneglycol- and saccharide-containing vinylethers. The cleavable covalent bond between the membrane active polymer and the polynucleotide may be reactive in the presence of acid or thiols. The membrane active polymer may promote polynucleotide entry into a cell through the plasma membrane or through disruption of endocytic membranes.

In a preferred embodiment, we describe polynucleotide transfection agents comprising: molecular conjugates of polynucleotides and membrane active polymers wherein the membrane active polymer is linked to the polynucleotide via labile or cleavable bond. The membrane active polymer may be selected from the list consisting of: amphipathic polymer, amphipathic polyvinylether, and membrane active peptide. The labile or cleavable bond may be selected from the list consisting of: pH-labile bonds, maleamate, acetal, enol ether, and disulfide bond. The polynucleotide may be selected from the list consisting of: single stranded polynucleotide, double stranded polynucleotide, DNA, RNA, oligonucleotide, expression vector, siRNA, microRNA, ribozyme, antisense polynucleotide and synthetic polynucleotide.

In a preferred embodiment, we describe the reversible modification of cationic membrane active polymer-polynucleotide conjugates to form anionic polymer-polynucleotide conjugates comprising: forming a polyamine-polynucleotide conjugate and modifying the amines on the polymer by reaction with maleic anhydrides. Modification of amines on the polymer by reaction with maleic anhydrides can reduce the membrane activity of the polymer. A preferred polyamine is a polyvinyl ether. A preferred maleic anhydride is a disubstituted maleic anhydride. A preferred disubstituted maleic anhydride is 2-propionic-3-methylmaleic anhydride. Exposure of the modified polyamine to acid, such as in an endosome, results in cleavage of the anhydride modification and regeneration of the amine. If the modification reduces membrane activity of the polymer, regeneration of the amines restores membrane activity.

In a preferred embodiment, the functionality of the membrane active polymer linked to the polynucleotide may be modified or enhanced by covalent attachment one or more functional groups. Functional groups may be added to the polymer though copolymerization or through reaction with a reactive group, such as an amine, in the polymer.

In a preferred embodiment, we describe a process for delivering a polynucleotide to a cell comprising: covalently linking the polynucleotide to a membrane active polymer via a labile or cleavable bond and contacting the cell with the polynucleotide-polymer conjugate. If the membrane active polymer contains an amine, the amine may be reversibly modified by reaction with a maleic anhydride. Reaction with a maleic anhydride may reduce or alter the charge on the polymer or add a functional group to the polymer. Modification of one or more amines on the membrane active polymer may reversibly inhibit the membrane activity of the polymer. A preferred linkage between the polynucleotide and polymer is through a maleic anhydride thioester.

Further objects, features, and advantages of the invention will be apparent from the following detailed description when taken in conjunction with the accompanying drawings.

DETAILED DESCRIPTION

Previous methods for delivery of oligonucleotides, including siRNA, to cells has relied upon complexation of the anionic oligonucleotide with a cationic delivery agent such as a cationic polymer or cationic lipid. However, because of the small size of oligo-nucleotides, complexes between oligonucleotides and polycations are inherently unstable. A more effective method for packaging the oligonucleotides is to covalently link the oligonucleotide to the delivery vehicle. However, in order for the oligonucleotide to be active, it must be released from the delivery vehicle. This release requires a labile bond between the oligonucleotide and the polymer that is broken after the polynucleotide is delivered to the cell.

Figure 1:
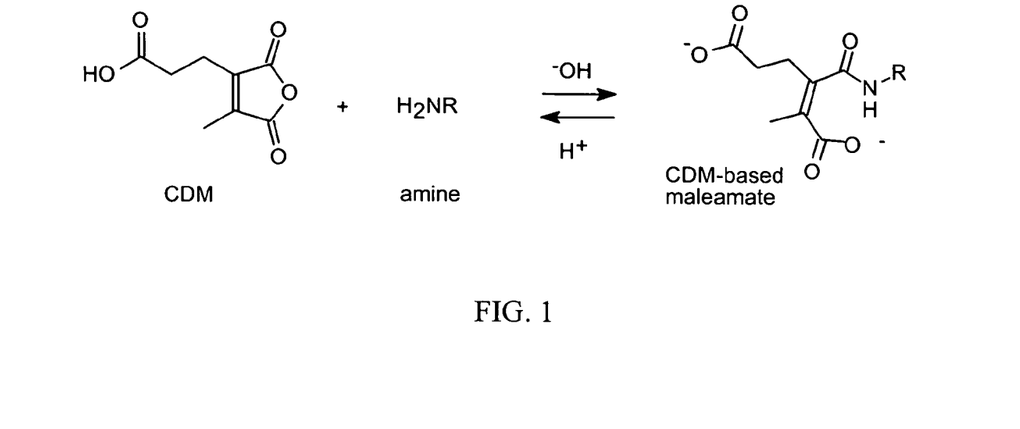
FIG. 1. Illustration of the reaction between carboxyl dimethylmaleic anhydride and an amine.

Disubstituted maleic anhydride derivatives can be effectively used to provide acid labile reversible covalent linkages between polynucleotides and delivery agent molecules. One disubstituted maleic anhydride derivative, Carboxylate substituted Dimethylmaleic anhydride (CDM) can be used to reversibly convert an amine into a carboxylate (FIG. 1). CDM contains a maleic anhydride functional group that may be converted into a pH-labile maleamate group, and a carboxylate group, which may be used for conjugation.

Figure 2:
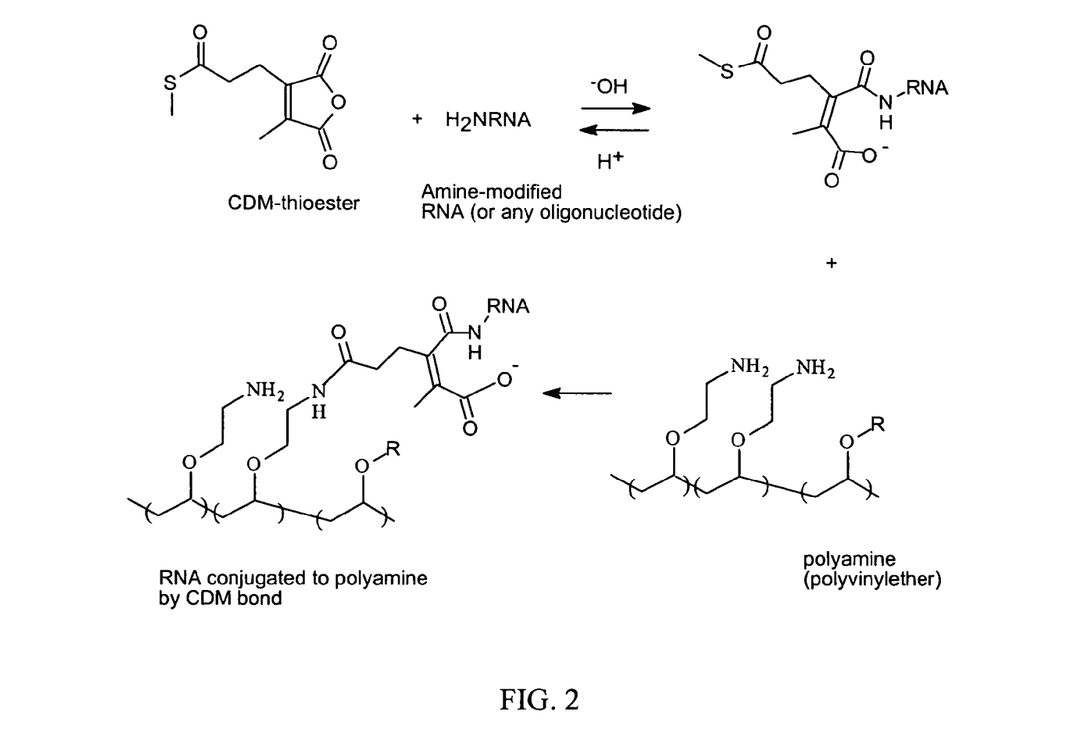
FIG. 2. Illustration of CDM-thioester reversible attachment of a polynucleotide to a polymer.

In order to conjugate selectively to the carboxylate group of CDM, it must be selectively activated in such a way as to react without reaction of the anhydride (or visa versa). This activation is achieved using a thioester ester group. Compared to an anhydride, the thioester group is relatively unreactive towards water and amines. Using a thioester derived from CDM (FIG. 2), it is possible to selectively react the anhydride functional group with an amine, followed by reaction with either an amine or an amine-terminal cysteine group. In this way, two molecules are attached via an acid-labile maleamate bond. More specifically, amine-modified polynucleotides may be reacted with a CDM thioester and then coupled to a polyamine.

Figure 3:
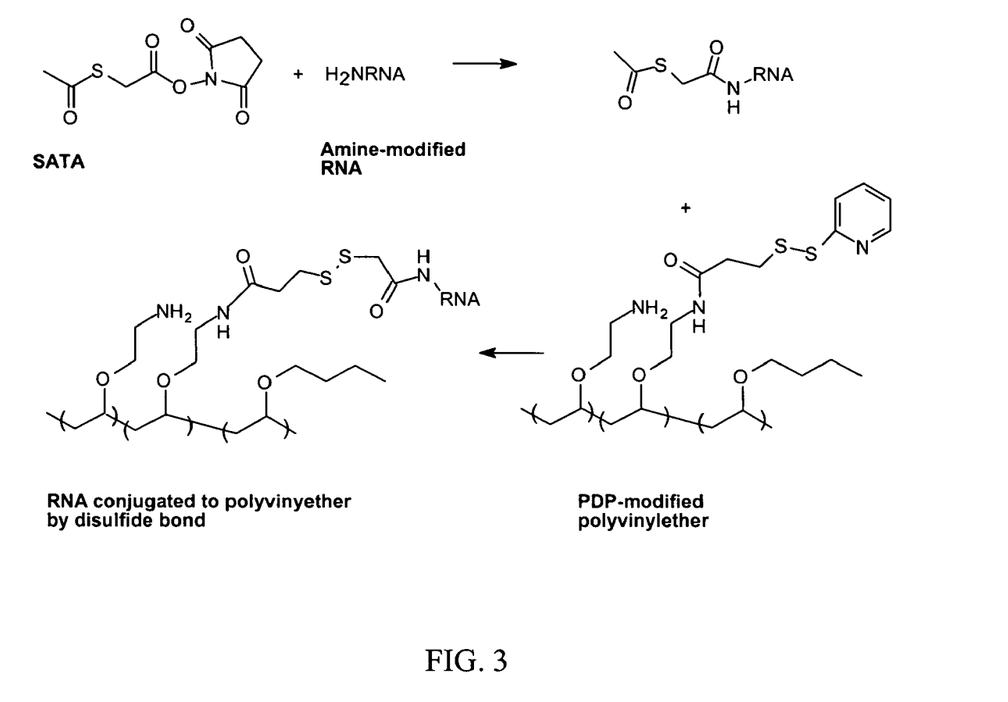
FIG. 3. Illustration of reversible conjugation of a polynucleotide and polyvinyl ether by a disulfide bond.

Another type of cleavable bond is a disulfide bond. An amine-containing polynucleotide can be modified with a reagent, such as N-succinimidyl-S-acetylthioacetate (SATA), that attaches a thioester to the polynucleotide. The polymer, a polyamine, is modified by attachment of a highly reactive disulfide bond containing group, such as 2-pyridyldithio (PDP). This group is selected such that the thioester of the modified polynucleotide will readily form a disulfide bond with the polymer. In the specific example illustrated in FIG. 3, addition of SATA-modified siRNA to a polyamine results in cleavage of the thioester by reaction with amine groups. This reaction results in the acylation of an amine and the production of a free thiol group on the siRNA. The resulting thiol-modified siRNA reacts with the PDP group on the polymer, resulting in the conjugation of siRNA and polymer by a disulfide bond.

Following conjugation of a polynucleotide to a membrane active polyamine, either by CDM or disulfide bond, any remaining amines on the polymer may be reacted with CDM to convert the cationic polyamine to a pH-sensitive polyacid (FIG. 1). Synthetic delivery vehicles designed for the in vivo delivery of nucleic acids often contain cationic polymers and/or lipids. However, positively charged agents have a tendency to be toxic following systemic administration and display low transfection efficiencies when used to deliver gene expression constructs. Toxic manifestations of systemically administered cationic nucleic acid complexes can range from red blood cell agglutination to potent inflammatory reaction and elevated serum levels of liver enzymes. Cationic complexes also tend to aggregate in physiological conditions and may accumulate in the capillary beds of the lung resulting in lethality. Furthermore, intravenously injected cationic nucleic acid complexes also encounter cells such as macrophages, monocytes, neutrophils, platelets, and erythrocytes, which are important potential mediators of immunity.

Polynucleotides are incapable of crossing biological membranes. In order for these compounds to enter cells, the cells must either take them up by endocytosis, into endosomes, or there must be a disruption of the cellular membrane to allow the compound to cross. In the case of endosomal entry, the endosomal membrane must be disrupted to allow for the entrance of the polynucleotide to the interior of the cell. Covalent attachment of a polynucleotide to a membrane active polymer provides for the co-delivery to the cell of the polynucleotide together with a membrane active compound. Furthermore, because the polynucleotide is attached to the polymer via a labile bond, the polynucleotide that is delivered to the cell is released from the polymer and has activity in the cell.

The present invention provides for delivery of polynucleotides to mammalian cells by conjugation of the polynucleotide to a membrane active polymer via a reversible linkage. The labile linkage groups are selected such that they undergo a chemical transformation (e.g., cleavage) when present in certain physiological conditions. The chemical transformation may be initiated by the addition of a compound to the cell or may occur spontaneously when introduced into intra- and/or extra-cellular environments (e.g., the lower pH conditions of an endosome or the extracellular space surrounding tumors). It is known in the art, that the conditions under which a labile group will undergo transformation can be controlled by altering the chemical constituents of the molecule containing the labile group. For example, addition of particular chemical moieties (e.g., electron acceptors or donors) near the labile group can affect the particular conditions (e.g., pH) under which chemical transformation will occur.

The present invention provides polynucleotide-polymer conjugates that are sufficiently chemically stable in pharmacologically acceptable solutions. Therefore, the conjugates can be prepared and delivered to cells in a solution that is not toxic to the cells. The conjugates can be added to the media in which cells are grown in vitro. Alternatively, the conjugates can be injected into a mammal for delivery of the polynucleotides to cells in vivo. For injection of the conjugates into a mammal, the conjugates may be inserted into a vessel or directly into a tissue. Other administration routes are also permissible. Under appropriate conditions, the labile bonds present in the polymer-polynucleotide conjugate undergo chemical transformation resulting in bond cleavage. In some embodiments of the present invention, polynucleotides are delivered to cells by polymer-polynucleotide conjugates that undergo chemical transformation when exposed to the low pH environment of an endosome. Cleavage of the bonds results in release of the polynucleotide from the polymer. Cleavage of the bonds can also result in re-activation of polymer membrane activity.

Renal ultrafiltration is one of the main routes of elimination from blood of hydrophilic proteins, polymers and polymer-protein conjugates. Among the parameters affecting this process are chemical composition, size, charge. In particular, size enlargement slows down kidney ultrafiltration and promotes the accumulation into permeable tissues by the passive enhanced permeation and retention mechanism. The molecular weight cut off for kidney elimination of native globular proteins is considered to be about 70 kDa, which is close to the molecular weight of serum albumin. PEG is a non-globular polymer for which renal clearance has been studied. Ultrafiltration of PEGs with molecular weight lower than 8 kDa is not restricted, whereas the elimination of PEGs in the range of 8-30 kDa is governed by the molecular size. With molecular weight exceeding 30 kDa, PEG elimination is dramatically slowed down. For this reason, polymer-polynucleotide conjugates in which the polymer is larger than about 10,000 daltons may be most effective for delivery of polynucleotides to cells in vivo. Also, anionic macromolecules have been found to be cleared by renal ultrafiltration and other pathways more slowly than neutral or positive ones reversible modification of positively charged groups on the polymer can be advantageous for delivery to cells in vivo.

The inclusion of labile bonds into membrane active polymers increases their versatility in a number of ways. It can reduce their toxicity by enabling their membrane activity to be expressed in specific tissues such as tumors and inflamed joints, specific sub-cellular locations such as endosomes and lysosomes, or under specific conditions such as a reducing environment. In one embodiment of the invention, the labile bonds are pH-sensitive in that the bonds break or are cleaved when pH of their microenvironment drops below the physiological pH of 7.4, or below pH of 6.5, or below pH of 5.5. In another embodiment, the labile bonds are disulfides that are labile under physiological conditions or that are cleaved by the addition of an exogenous reducing agent. Examples of labile bonds include: acetals, ketals, enol ethers, enol esters, amides of 2,3-disubstituted maleamic acid (maleamates), imines, imminiums, enamines, silyl ethers, and silyl enol ethers.

The invention specifies compounds of the following general structure: A-B-C wherein A is a biologically active compound; B is a labile linkage that contains a labile bond such as a pH labile bond; and, C is a membrane active polymer. The biologically active compound may be modified to enable attachment of the labile linkage onto the compound. If the biologically active compound is a polynucleotide, the polynucleotide may be modified to contain a reactive group at the 3' or 5' terminus. Alternatively, the polynucleotide may be modified though alkylation to contain a reactive group. Specifically, nitrogen and sulfur mustards may be used to alkylate polynucleotides. Biologically active compounds may be selected from the list comprising: pharmaceuticals, drugs, proteins, peptides, hormones, cytokines, enzymes and polynucloetides such as anti-sense, ribozyme, siRNA, recombining nucleic acids, and expressed genes. pH-labile bonds may be selected from the list comprising: acetals, ketals, enol ethers, enol esters, amides of 2,3-disubstituted maleamic acids, imines, imminiums, enamines, silyl ethers, and silyl enol ethers.

Definitions:

Labile Bond—A labile bond is a covalent bond that is capable of being selectively broken. That is, the labile bond may be broken in the presence of other covalent bonds without the breakage of the other covalent bonds. For example, a disulfide bond is capable of being broken in the presence of thiols without cleavage of other bonds which may also be present in the molecule, such as carbon-carbon, carbon-oxygen, carbon-sulfur and carbon-nitrogen bonds.

pH sensitivity can be broadly defined as any change in polymer's physico-chemical properties over a defined range of pH. A more narrow definition demands significant changes in the polymer in a physiologically tolerated pH range (usually pH 5.5-8). Polyions can be divided into three categories based on their ability to donate or accept protons in aqueous solutions: polyacids, polybases and polyampholytes. Use of pH-sensitive polyacids in drug delivery applications usually relies on their ability to become soluble with increased pH (acid/salt conversion), to form complexes with other polymers over a change of pH, or to undergo significant change in hydrophobicity/hydrophilicity balance. Combinations of all three above factors are also possible.

pH-Labile Linkages and Bonds—pH-labile refers to the selective breakage of a covalent bond under acidic conditions (pH<7). That is, the pH-labile bond may be broken under acidic conditions in the presence of other covalent bonds that are not broken. The term pH-labile includes both linkages and bonds that are pH-labile, very pH-labile, and extremely pH-labile.

Very pH-Labile Linkages and Bonds—A subset of pH-labile bonds is very pH-labile. For the purposes of the present invention, a bond is considered very pH-labile if the half-life for cleavage at pH 5 is less than 45 minutes.

Extremely pH-Labile Linkages and Bonds—A subset of pH-labile bonds is extremely pH-labile. For the purposes of the present invention, a bond is considered extremely pH-labile if the half-life for cleavage at pH 5 is less than 15 minutes.

Amphiphilic and Amphipathic Compounds—Amphipathic, or amphiphilic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Polymer—A polymer is a molecule built up by repetitive bonding together of smaller units called monomers. A polymer can be linear, branched network, star, comb, or ladder types of polymer. A polymer can be a homopolymer in which a single monomer is used or can be copolymer in which two or more monomers are used.

The main chain of a polymer is composed of the atoms whose bonds are required for propagation of polymer length. For example in poly-L-lysine, the carbonyl carbon, α-carbon, and α-amine groups are required for the length of the polymer and are therefore main chain atoms. The side chain of a polymer is composed of the atoms whose bonds are not required for propagation of polymer length.

Other Components of the Monomers and Polymers: Polymers may have functional groups that enhance their utility. These groups can be incorporated into monomers prior to polymer formation or attached to the polymer after its formation. Functional groups may be selected from the list consisting of: targeting groups, interaction modifiers, steric stabilizers, and membrane active compounds, and affinity groups.

Targeting groups—Targeting groups, or ligands, are used for targeting the polymer or polymer complex to cells, to specific cells, to tissues or to specific locations in a cell. Targeting groups enhance the association of molecules with a cell. Examples of targeting groups include those that target to the asialoglycoprotein receptor by using asialoglycoproteins or galactose residues. Other proteins such as insulin, EGF, or transferrin can be used for targeting. Other targeting groups include molecules that interact with membranes such as fatty acids, cholesterol, dansyl compounds, and amphotericin derivatives. A variety of ligands have been used to target drugs and genes to cells and to specific cellular receptors. The ligand may seek a target within the cell membrane, on the cell membrane or near a cell. Binding of a ligand to a receptor may initiate endocytosis.

Steric stabilizer—A steric stabilizer is a long chain hydrophilic group that prevents aggregation of final polymer by sterically hindering particle to particle electrostatic interactions. Examples include: alkyl groups, PEG chains, polysaccharides, hydrogen molecules, alkyl amines.

Interaction modifier—An interaction modifier changes the way that a molecule interacts with itself or other molecules, relative to molecule containing no interaction modifier. The result of this modification is that self-interactions or interactions with other molecules are either increased or decreased. For example, polyethylene glycol is an interaction modifier that decreases interactions between molecules and themselves and with other molecules.

Membrane active—Membrane active polymers or compounds are molecules that are able to inducing one or more of the following effects upon a biological membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. More specifically membrane active compounds allow for the transport of molecules with molecular weight greater than 50 atomic mass units to cross a membrane. This transport may be accomplished by either the loss of membrane structure or the formation of holes or pores in the membrane.

Membrane active polymers may be selected from the list comprising: membrane active toxins such as pardaxin, melittin, cecropin, magainin, PGLa, indolicidin, and dermaseptin; synthetic amphipathic peptides; and amphipathic polymers such as butyl polyvinyl ether. There exists little to no homology or structural similarity between all the different membrane active peptides. Therefore, they are defined by their membrane activity.

Polyion—A polyion (or polyelectrolyte), is a polymer possessing charge, i.e. the polymer contains a group (or groups) that has either gained or lost one or more electrons. The term polyion includes polycations, polyanions, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

Polycation—A polycation can be a polymer possessing net positive charge. A polymeric polycation can contain monomer units that are charge positive, charge neutral, or charge negative, however, the net charge of the polymer must be positive. A polycation also can be a non-polymeric molecule that contains two or more positive charges.

Polyanion—A polyanion can be a polymer containing a net negative charge. A polymeric polyanion can contain monomer units that are charge negative, charge neutral, or charge positive, however, the net charge on the polymer must be negative. A polyanion can also be a non-polymeric molecule that contains two or more negative charges.

Polynucleotide—The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications that place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (mRNAs) are small noncoding polynucleotides, about 22 nucleotides long, that direct destruction or translational repression of their mRNA targets. Antisense polynucleotides comprise sequence that is complimentary to an gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Biologically active compound—A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. Biologically active compounds may be selected from the group comprising: pharmaceuticals, proteins, peptides, polypeptides, hormones, cytokines, antigens, viruses, oligonucleotides, and nucleic acids.

Transfection—The process of delivering a polynucleotide to a cell has been commonly termed transfection or the process of transfecting and also it has been termed transformation. The term transfecting as used herein refers to the introduction of a polynucleotide or other biologically active compound into cells. The polynucleotide may be delivered to the cell for research purposes or to produce a change in a cell that can be therapeutic. The delivery of a polynucleotide for therapeutic purposes is commonly called gene therapy. Gene therapy is the purposeful delivery of genetic material to somatic cells for the purpose of treating disease or biomedical investigation. The delivery of a polynucleotide can lead to modification of the genetic material present in the target cell. The term stable transfection or stably transfected generally refers to the introduction and integration of an exogenous polynucleotide into the genome of the transfected cell. The term stable transfectant refers to a cell which has stably integrated the polynucleotide into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of a polynucleotide into a cell where the polynucleotide does not integrate into the genome of the transfected cell. If the polynucleotide contains an expressible gene, then the expression cassette is subject to the regulatory controls that govern the expression of endogenous genes in the chromosomes. The term transient transfectant refers to a cell which has taken up a polynucleotide but has not integrated the polynucleotide into its genomic DNA.

EXAMPLES

Example 1

Synthesis of a vinyl ether monomer: 2-Vinyloxy Ethyl Phthalimide was prepared via reacting 2-chloroethyl vinyl ether (25 g, 0.24 mol) and potassium phthalimide (25 g, 0.135 mol) in 100° C. DMF (75 mL) using tetra n-butyl ammonium bromide (0.5 g) as the phase transfer catalyst. This solution was heated for six hours and then crashed out in water and filtered. This solid was then recrystallized twice from methanol to give white crystals.

Example 2

General synthesis of membrane active polyvinyl ether polymers. X mol % amine-protected vinylether (e.g., 2-Vinyloxy Ethyl Phthalimide) was added to an oven dried round bottom flask under a blanket of nitrogen in anhydrous dichloromethane. To this solution Y mol % alkyl (e.g., ethyl, propyl, butyl) vinylether was added, followed by Z mol % alkyl (dodecyl, octadecyl) vinylether. While the polymers detailed are derived from 2-3 different monomers, the invention is not limited to a specific composition of vinyl ether monomers. Polymers comprising more monomers or different monomers were readily envisioned. The solution was brought to −78° C. in a dry ice acetone bath. To this solution 10 mol % $BF_3EtOEt$ was added and the reaction was allowed to proceed for 2-3 hours at −78° C., and then quenched with a methanol ammonium hydroxide solution. The polymer was brought to dryness under reduced pressure and then brought up in 30 ml of 1,4-dioxane/methanol (2/1). 20 mol eq. of hydrazine per phthalimide was added to remove the protecting group from the amine. The solution was refluxed for 3 hours, then brought to dryness under reduced pressure. The solid was brought up in 20 ml 0.5 M HCl, refluxed for 15 minutes, diluted with 20 ml distilled water, and refluxed for additional hour. The solution was then neutralized with NaOH, cooled to room temperature, transferred to 3,500 molecular cellulose tubing, dialyzed for 24 hrs (2×20L) against distilled water, and freeze dried. The molecular weight of the polymers was estimated using analytical size exclusion columns according to standard procedures. While polymers containing the indicated vinyl ether monomers are described in these examples, the invention is not limited to these particular monomers.

After removal of the phthalimide groups by sequential treatment with hydrazine and HCl, the polymers were transfer to 3,500 molecular cellulose tubing and dialyzed for 24 h (2×20L) against distilled water, and freeze dried. The polymers were then dissolved in water and placed onto a sephadex G-15 column. The polymers that were excluded from sephadex G-15 were isolated and concentrated by lyophilization. The molecular weights of the polymers were then determined by GPC using Eprogen Inc. CATSEC100, CATSEC300, and CATSEC100 columns in series. The running buffer was 50 mM NaCl, 0.1% TFA, and 10% MeOH. Polyvinylpyridine standards were used as the calibration curve. The molecular weights of the polymers were in the range 10,000-100,000, with the majority of polymer preparations over 20,000.

Example 3

Synthesis of 2-propionic-3-methylmaleic anhydride (carboxydimethylmaleic anhydride or CDM). To a suspension of sodium hydride (0.58 g, 25 mmol) in 50 mL anhydrous tetrahydrofuran was added triethyl-2-phosphonopropionate (7.1 g, 30 mmol). After evolution of hydrogen gas had stopped, dimethyl-2-oxoglutarate (3.5 g, 20 mmol) in 10 mL anhydrous tetrahydrofuran was added and stirred for 30 minutes. Water, 10 mL, was then added and the tetrahydrofuran was removed by rotary evaporation. The resulting solid and water mixture was extracted with 3×50 mL ethyl ether. The ether extractions were combined, dried with magnesium sulfate, and concentrated to a light yellow oil. The oil was purified by silica gel chromatography elution with 2:1 ether: hexane to yield 4 g (82% yield) of pure triester. The 2-propionic-3-methylmaleic anhydride was then formed by dissolving of this triester into 50 mL of a 50/50 mixture of water and ethanol containing 4.5 g (5 equivalents) of potassium hydroxide. This solution was heated to reflux for 1 hour. The ethanol was then removed by rotary evaporation and the solution was acidified to pH 2 with hydrochloric acid. This aqueous solution was then extracted with 200 mL ethyl acetate, which was isolated, dried with magnesium sulfate, and concentrated to a white solid. This solid was then recrystallized from dichloromethane and hexane to yield 2 g (80% yield) of 2-propionic-3-methylmaleic anhydride.

Thioesters, esters and amides may be synthesized from CDM by conversion of CDM to its acid chloride with oxalyl chloride followed by the addition of a thiol, ester or amine and pyridine.

Example 4

Delivery of siRNA by Conjugation to Membrane Active Polymer by a CDM or Disulfide Labile Linkage Disulfide Conjugate: 50 ng of siRNA targeted against luciferase that had a 5'-amino group on the sense strand was reacted with 1 µg of N-succinimidyl-S-acetylthioacetate in the presence of HEPES base pH 7.5. Separately, 50 µg of a polyvinyl ether synthesized from a 50/50 mixture of amine-protected and butyl vinyl ether monomers was reacted with 5 µg of 3-(2-pyridyldithio)propionic acid N-hydroxysuccinimide ester in the presence of HEPES pH 7.5. The modified siRNA and modified polymer were then combined to allow covalent attachment of the siRNA to the polymer. After 6-24 hours, the polymer-siRNA conjugate was reacted with 200 µg of 2-propionic-3-methylmaleic anhydride in the presence of HEPES base. The particles were added to a mouse hepatocyte HEPA cell line that stably expresses the luciferase gene. As a control, samples containing CDM-modified polymer (without siRNA) were added to cells. In cells exposed to the polymer-polynucleotide conjugate, luciferase expression was suppressed 75% relative to cells exposed to polymer alone, indicating delivery of functional siRNA to the cells.

CDM Conjugate: 50 ng of siRNA targeted against luciferase that had a 5'-amino group on the sense strand was reacted with 2 µg of CDM thioester in the presence of HEPES pH 7.9. To the siRNA was added 50 µg of a polyvinyl ether synthesized from a 50/50 mixture of amine-protected and butyl vinyl ether monomers. After 6-24 hours, the polymer-siRNA conjugate was reacted with 200 µg of 2-propionic-3-methylmaleic anhydride in the presence of HEPES base. The particles were added to a mouse hepatocyte HEPA cell line that stably expresses the luciferase gene. As a control, samples containing CDM-modified polymer (without siRNA) were added to cells. In cells exposed to the polymer-polynucleotide conjugate, luciferase expression was suppressed 86% relative to cells exposed to polymer alone, indicating delivery of functional siRNA to the cells.

TABLE 1

Percent inhibition of luciferase activity following transfection of HEPA-Luc cells using membrane active polymer-siRNA conjugates.

| Disulfide Conjugation | CDM Conjugation |
|---|---|
| 75% | 86% |

Example 5

The delivery of phosphorodiamidate morpholino oligonucleotide (PMO) to cells using polymer-PMO conjugates. Using the CDM-thioester based crosslinking used to link siRNA and polymer, it is also possible to reversibly conjugate other types of oligonucleotides to polymers. In particular, we studied the delivery of PMO to cells. 5 nmol of amino-PMO (which blocks a mutant splice site in the mutant Luciferase transcript) either bare or hybridized with a complimentary strand of DNA was reacted with nothing or with 2 µg of CDM thioester in the presence of HEPES pH 7.9. To this was added 200 µg of polyvinyl ether synthesized from 50% amino vinylether, 45% butyl vinylether and 5% dodecylvinylether (DW550). After three or more hours the polymer+PMO or polymer-PMO conjugate was reacted with 500 µg of CDM in the presence of HEPES to maintain pH>7.5. In addition to CDM, the conjugates were reacted with PEG esters of CDM, which are derived from the acid chloride of CDM and PEG monomethyl ethers of various molecular weights. The conjugates were then added HeLa Luc/705 cells (Gene Tools, Philomath OR) grown under conditions used for HeLa cells. The cells were plated in 24-well culture dishes at a density of $3 \times 10^6$ cells/well and incubated for 24 hours. Media were replaced with 1.0 ml DMEM containing 2.5 nmol amino-PMO complexes. The cells were incubated for 4 hours in a humidified, 5% $CO_2$ incubator at 37° C. The media was then replaced with DMEM containing 10% fetal bovine serum. The cells were then incubated for an additional 48 h. The cells were then harvested and the lysates were then assayed for luciferase expression. The results demonstrate enhanced delivery of the uncharged polynucleotide when the transfection agent is a DW550 polyvinylether polymer-PMO conjugate.

TABLE 2

Delivery of uncharged polynucleotides to cells

| Transfection vehicle | Fold induction of luciferase |
|---|---|
| no linkage | |
| DW550 + bare PMO | 2 |
| DW550 + PMO hybridized with DNA | 2 |
| polymer-PMO conjugate | |
| DW550 – CDM – barePMO | 7.5 |
| DW550 – CDM – hybridized PMO | 10 |

Example 6

Figure 4:
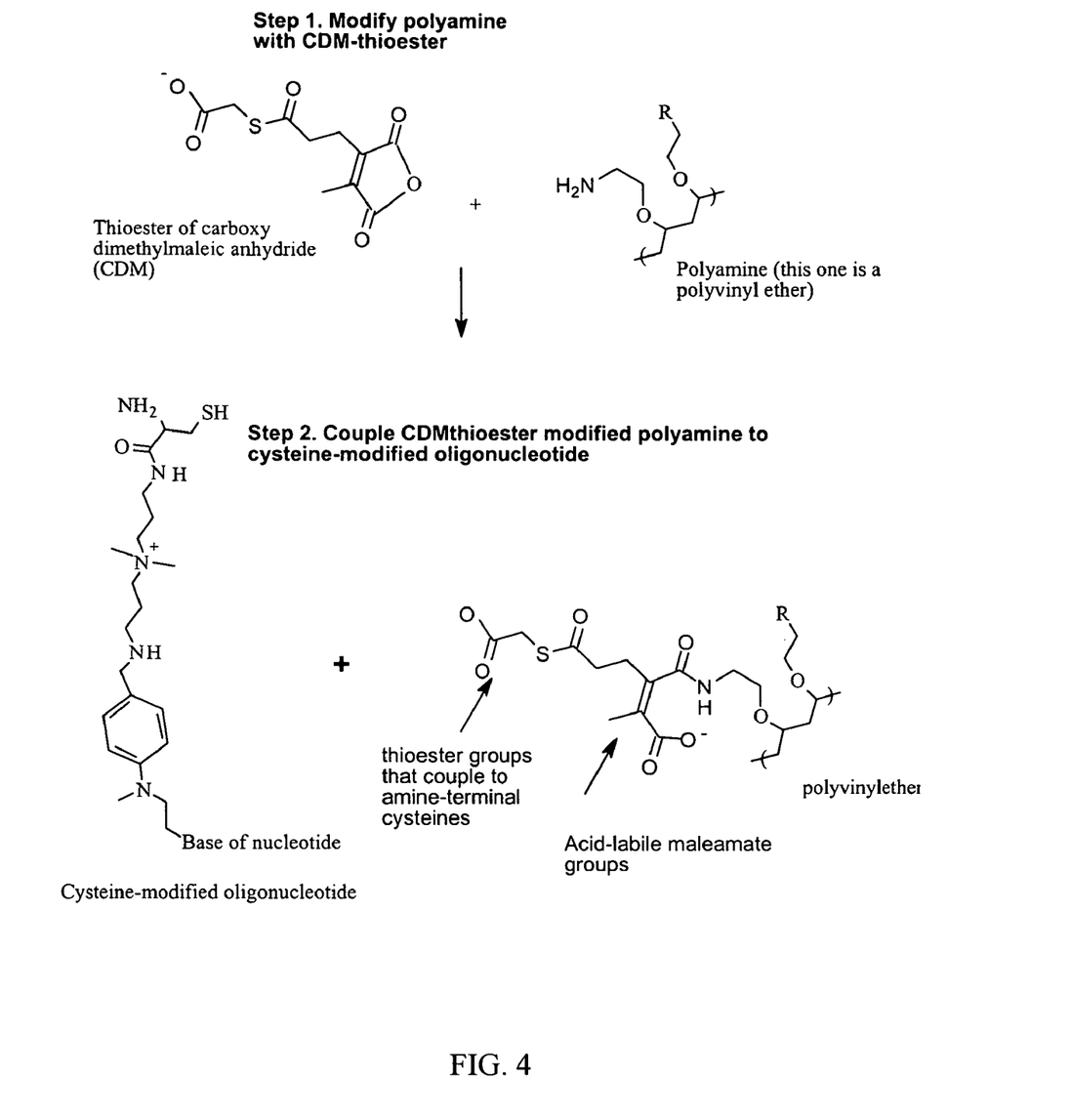
FIG. 4. Illustration of conjugation of a cysteine-modified polynucleotide to a polyamine via an acid labile CDM-thioester linkage.

The postsynthetic modification of siRNA for attachment of siRNA to delivery polymer. In order to modify an oligonucleotide, such as siRNA, with a thioester, the amine may be attached during or after nonenzymatic synthesis. In the previous examples, an amine modification was attached during synthesis of the polynucleotide. Post-synthetic modification may be achieved using an aromatic nitrogen mustard reagent (U.S. Pat. No. 6,262,252). Oligonucleotide-polymer coupling may be achieved by modification of a polynucleotide with an aromatic nitrogen mustard containing a pyridyldithio-protected cysteine group and reacting the cysteine group with a thioester that is reversibly attached to a polymer as illustrated in FIG. 4.

In these examples, thioesters attached to amine-containing membrane active polymers were reacted with cysteines on siRNAs specific to the luciferase gene to form the polymer-siRNA conjugate transfection agents. The thioesters were attached to the polymers by pH-labile maleamate bonds. As a consequence the siRNAs were attached to the polymers via pH-labile bonds. Remaining amines on the polymers were then reacted with CDM alter the charge on the polymers and reversible inhibit membrane activity of the polymers.

Two amine-containing polymers were reversibly attachment to siRNA: a synthetic polymer and a synthetic peptide containing the same amino acid sequence as a naturally occurring peptide. The synthetic polymer was an amphiphilic cationic polyvinyl ether. Amphiphilicity is derived from the inclusion of hydrophobic vinyl ethers. In this example, the polymer linked to the siRNA, DW459A, contained a 1:1 mixture of amine and butyl groups ($R = n-C_4H_9$). The naturally occurring peptide was pardaxin, a toxin from fish, which has the sequence GFFALIPKIISSPLFKTLLSAVG-SALSSSGEQE (SEQ ID NO. 1).

Conjugation to Polymer: 50 ng of siRNA targeted against luciferase was reacted with 50 ng of Label IT™ cysteine. Separately, 50 µg of a polyvinyl ether synthesized from a 50/50 mixture of amine-protected and butyl vinyl ether monomers was reacted with 0, 2.5, 5, or 20 µg of CDM-thioester mixed with 250, 247.5, 245, or 230 µg CDM. Increasing levels of CDM-thioester modification allows increasing amounts of polynucleotide to be linked to the polymer. The cysteine-modified siRNA was then added to the thioester modified polymer. The conjugates were added to a mouse hepatocyte HEPA cell line that had been transfected with the Renilla and firefly luciferase genes. The siRNA is known to specifically inhibit expression of the firefly luciferase gene. As a control, samples containing CDM-modified polymer (without siRNA) were added to cells. The firefly and Renilla luciferase activities were measured and the firefly to Renilla luciferase expression level ratio was determined. A decrease in the ratio relative to no siRNA control cells indicates specific firefly luciferase knockout due to the delivery of functional siRNA.

TABLE 3

Delivery of siRNA to mammalian cell in vitro using polyvinyl ether-siRNA conjugates.

| Percent thioester modification* | Percent inhibition of firefly luciferase |
|---|---|
| 0 | 0.27 |
| 1 | 0.25 |
| 2 | 0.47 |
| 4 | 0.47 |

*Mole percent is relative the number of amine groups on DW459A

Conjugation to peptide: 50 ng of siRNA targeted against firefly luciferase was reacted with 50 ng of Label IT™ cysteine. Separately, 50 µg of pardaxin was reacted with 0, 5, 10, or 20 µg of CDM thioester mixed with 250, 245, 240, or 230 µg CDM. Increasing levels of CDM-thioester modification allows increasing amounts of polynucleotide to be linked to the polymer. The cysteine-modified siRNA was then added to the thioester modified peptide. The conjugates were added to a mouse hepatocyte HEPA cell line that had been transfected with the Renilla and firefly luciferase genes. As a control, samples containing CDM-modified polymer (without siRNA) were added to cells. The firefly and Renilla luciferase activities were measured and the firefly to Renilla luciferase expression level ratio was determined. A decrease in the ratio relative to no siRNA control cells indicates specific firefly luciferase knockout due to the delivery of siRNA.

TABLE 4

Delivery of siRNA to mammalian cell in vitro using Pardaxin-siRNA conjugates.

| Weight percent thioester modification* | Percent inhibition of firefly luciferase |
|---|---|
| 0 | 0.23 |
| 10 | 0.20 |
| 20 | 0.47 |
| 40 | 0.73 |

*Weight percent of CDM-thioester to pardaxin.

One can observe that there was a dependence of siRNA delivery on the amount of thioester modification of the polyvinylether and the peptide pardaxin, and therefore, the reversible attachment of the siRNA to the delivery reagents enhanced delivery efficiencies.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

---

---

We claim:

1. A composition for delivering a polynucleotide to a mammalian cell in vivo comprising: a reversibly-modified membrane active polyamine-polynucleotide conjugate wherein:
   a) the reversibly-modified membrane active polyamine is linked to the polynucleotide via a labile covalent bond; and,
   b) the reversibly-modified membrane active polyamine consists of a negatively charged polymer that is not membrane active wherein the negative charge comes from a plurality of carboxyl groups linked to the polymer via pH-labile covalent linkages wherein cleavage of the pH-labile covalent bonds in response to a decrease in pH results in cleavage of the carboxyl groups from the polymer and formation of amine groups thereby forming a membrane active polyamine, and wherein c) the membrane active polyamine has a molecular weight greater than 10,000 daltons.

2. The composition of claim 1 wherein the polynucleotides consists of an oligonucleotide.

3. The composition of claim 2 wherein the polynucleotide is selected from the group consisting of: dsRNA, siRNA, microRNA, siRNA expression cassette, antisense oligonucleotide and ribozyme.

4. The composition of claim 1 wherein the membrane active polyamine consists of a polyvinyl ether.

5. The composition of claim 1 wherein the membrane active polyamine consists of an amphipathic polymer.

6. A composition for delivering a biologically active compound to a mammalian cell in vivo comprising: a reversibly-modified membrane active polyamine-biologically active compound conjugate wherein:

a) the reversibly-modified membrane active polyamine is linked to the biologically active compound via a labile covalent bond; and, b) the reversibly-modified membrane active polyamine consists of a negatively charged polymer that is not membrane active wherein the negative charge comes from a plurality of carboxyl groups linked to the polymer via pH-labile covalent linkages wherein cleavage of the pH-labile covalent bonds in response to a decrease in pH results in cleavage of the carboxyl groups from the polymer and formation of amine groups thereby forming a membrane active polyamine; and wherein c) the membrane active polyamine has a molecular weight greater than 10,000 daltons.

7. The composition of claim 6 wherein the biologically active compound comprises a polynucleotide.

8. The composition of claim 7 wherein the polynucleotides consists of an oligonucleotide.

9. The composition of claim 8 wherein the polynucleotide is selected from the group consisting of: dsRNA, siRNA, microRNA, siRNA expression cassette, antisense oligonucleotide and ribozyme.

10. The composition of claim 6 wherein the membrane active polyamine consists of an amphipathic polymer.

11. The composition of claim 6 wherein the membrane active polyamine consists of a polyvinyl ether.

12. A method for delivering a polynucleotide to a mammalian cell in vivo comprising:

a) attaching the biologically polynucleotide to an amphipathic membrane active polyamine having a molecular weight greater than 10,000 daltons via a labile bond to form a conjugate, b) reversibly modifying a plurality of amines on the amphipathic membrane active polyamine by covalent attachment of carboxyl groups to the amines via very pH-labile bonds to form a negatively charged polymer that is not membrane active wherein cleavage of the pH-labile covalent bonds in response to a decrease in pH results in cleavage of the carboxyl groups from the polymer and formation of amine groups thereby regenerating the amphipathic membrane active polyamine; and, c) contacting the cell with the conjugate.

13. The method of claim 12 wherein the polynucleotide is selected from the group consisting of: dsRNA, siRNA, microRNA, siRNA expression cassette, antisense oligonucleotide and ribozyme.

* * * * *

SEQUENCE LISTING

<160> NUMBER OF SEQ ID NOS: 1

<210> SEQ ID NO 1
<211> LENGTH: 33
<212> TYPE: PRT
<213> ORGANISM: Pardachirus marmoratus

<400> SEQUENCE: 1

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu